United States Patent
Li et al.

(10) Patent No.: US 9,649,492 B2
(45) Date of Patent: May 16, 2017

(54) VARIABLE FREQUENCY STIMULATION THERAPY METHOD AND IMPLANTABLE MEDICAL DEVICE

(71) Applicant: Tsinghua University, Beijing (CN)

(72) Inventors: Lu-Ming Li, Beijing (CN); Fu-Min Jia, Beijing (CN); Xing Qian, Beijing (CN); Sen Wan, Beijing (CN); Hong-Wei Hao, Beijing (CN)

(73) Assignee: Tsinghua University, Beijing (CN)

( * ) Notice: Subject to any disclaimer, the term of this patent is extended or adjusted under 35 U.S.C. 154(b) by 1 day.

(21) Appl. No.: 14/700,073

(22) Filed: Apr. 29, 2015

(65) Prior Publication Data
US 2016/0184589 A1   Jun. 30, 2016

(30) Foreign Application Priority Data
Dec. 31, 2014 (CN) .......................... 2014 1 0849266

(51) Int. Cl.
*A61N 1/36* (2006.01)
*A61N 1/372* (2006.01)

(52) U.S. Cl.
CPC ..... *A61N 1/36067* (2013.01); *A61N 1/36146* (2013.01); *A61N 1/36171* (2013.01); *A61N 1/36189* (2013.01); *A61N 1/37264* (2013.01)

(58) Field of Classification Search
CPC .................................................. A61N 1/36178
See application file for complete search history.

(56) References Cited

U.S. PATENT DOCUMENTS

| | | | | |
|---|---|---|---|---|
| 4,739,764 | A * | 4/1988 | Lue | A61N 1/36007 607/40 |
| 5,593,432 | A * | 1/1997 | Crowther | A61N 1/36021 607/46 |
| 5,800,476 | A * | 9/1998 | Piunti | A61N 1/326 607/66 |
| 6,321,119 | B1 * | 11/2001 | Kronberg | A61N 1/326 607/66 |
| 6,662,051 | B1 * | 12/2003 | Eraker | A61N 1/37282 607/59 |
| 2004/0111127 | A1 * | 6/2004 | Gliner | A61N 1/36167 607/45 |
| 2006/0149337 | A1 * | 7/2006 | John | A61N 1/36082 607/45 |
| 2007/0021801 | A1 * | 1/2007 | Heruth | A61M 5/14276 607/46 |
| 2010/0069995 | A1 * | 3/2010 | Danielsson | A61N 1/36114 607/50 |

(Continued)

*Primary Examiner* — Kennedy Schaetzle
(74) *Attorney, Agent, or Firm* — Steven Reiss

(57) ABSTRACT

The disclosure relates to an electrical stimulation therapy method. The method includes applying a variable frequency stimulation pulse to target nerve tissue of the patient, wherein the variable frequency stimulation pulse comprises at least two kinds of electrical stimulation pulse trains at different frequencies; the at least two kinds of electrical stimulation pulse trains alternately stimulate target nerve tissue and form a plurality of pulse train periods; and each of the at least two kinds of alternate electrical stimulation pulse trains in each of the plurality of pulse train periods has a duration in a range from about 0.1 seconds to about 60 minutes. An implantable medical device for generating the variable frequency stimulation pulse is also related.

22 Claims, 14 Drawing Sheets

(56) References Cited

U.S. PATENT DOCUMENTS

2010/0152807 A1* 6/2010 Grill ................. A61N 1/36082
607/45
2012/0136410 A1* 5/2012 Rezai ................ A61N 1/36067
607/45

* cited by examiner

VARIABLE FREQUENCY STIMULATION THERAPY METHOD AND IMPLANTABLE MEDICAL DEVICE

CROSS-REFERENCE TO RELATED APPLICATIONS

This application claims all benefits accruing under 35 U.S.C. §119 from China Patent Applications: Application No. 201410849266.3, filed on Dec. 31, 2014, in the China Intellectual Property Office, disclosures of which are incorporated herein by references.

FIELD

The subject matter herein generally relates to therapy methods and medical devices, especially an variable frequency electrical stimulation therapy and an implantable medical device.

BACKGROUND

Implantable medical devices, such as cardiac pacemakers, defibrillators, deep brain stimulators, spinal cord stimulators, vagus nerve stimulators, stomach stimulators, muscle stimulators, or peripheral nerve stimulators, are widely used for disease therapy.

The implantable medical device can generate electrical stimulation pulses and apply the electrical stimulation pulses to the target nerve tissue of the patient to treat a disease. Usually, the implantable medical device stimulates the target nerve tissue at a constant frequency for a long time, such as several days, several months, or even several years, and that is called constant frequency stimulation mode. However, the constant frequency stimulation mode has a low efficacy for some disorders and would result in adaptability to stimulation therapy. In the case of patients suffering from Parkinson's disease (Parkinson patients) for example, deep brain stimulation at constant frequency stimulation mode has little treatment efficiency on some non-motor symptoms, such as dysarthria, dyskinesia or freezing of gait. For Parkinson patients and some epilepsy sufferers, it is easy to adapt to the electrical stimulation of the nerves at constant frequency stimulation mode, like constant exposure to a drug results in resistance to the action of the drug and treatment can be ineffective.

An electrical stimulation testing device can be used to test whether a patient is suitable for the electrical stimulation therapy. However, an electrical stimulation testing device only has the constant frequency stimulation mode.

What is needed, therefore, is to provide an electrical stimulation therapy method and an implantable medical device which can overcome the shortcomings as described above.

BRIEF DESCRIPTION OF THE DRAWINGS

Implementations of the present technology will now be described, by way of example only, with reference to the attached figures, wherein.

DETAILED DESCRIPTION

Figure 1:
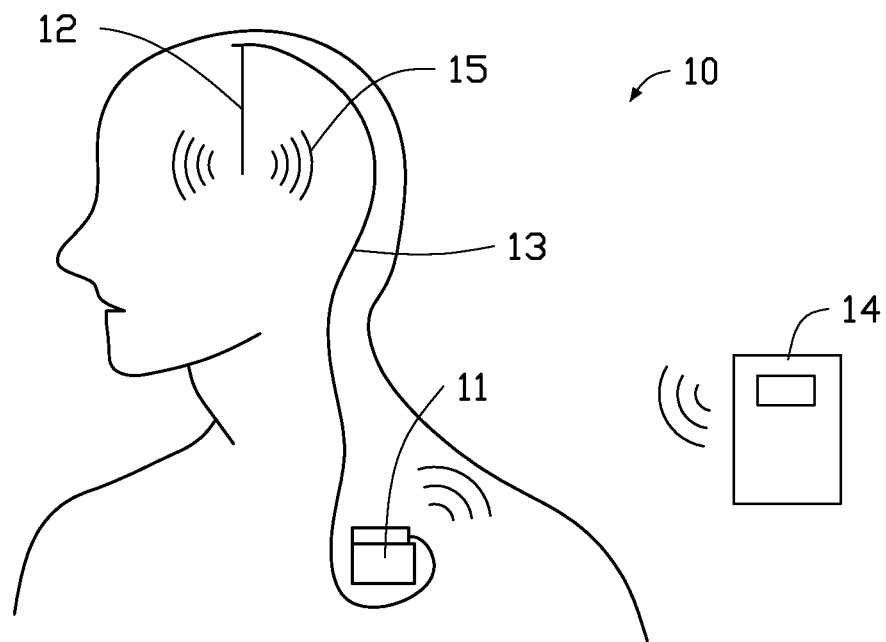
FIG. 1 is a schematic view of one embodiment of an implantable medical device.

It will be appreciated that for simplicity and clarity of illustration, where appropriate, reference numerals have been repeated among different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

References will now be made to the drawings to describe, in detail, various embodiments of the electrical stimulation therapy methods and the implantable medical devices. The implantable medical device can be a cardiac pacemaker, a defibrillator, a deep brain stimulator, a spinal cord stimulator, a vagus nerve stimulator, a stomach stimulator, a muscle stimulator, or a peripheral nerve stimulator. In this case, the implantable deep brain stimulator is used as an illustration of the implantable medical device.

As shown in FIG. 1, the implantable deep brain stimulator 10 of one embodiment usually includes a pulse generator 11, a lead 12, a wire 13, and a programmer 14.

The pulse generator 11 is configured to generate electrical stimulation pulses 15 and deliver the electrical stimulation pulses 15 to the lead 12 through the wire 13. The programmer 14 is electrically connected to the pulse generator 11 wirelessly and configured to control the pulse generator 11. The lead 12 is configured to apply the electrical stimulation pulses 15 to the target nerve tissue of the patient. The lead 12 includes at least one stimulation contactor (not shown). After the lead 12 is implanted in body, the at least one stimulation contactor contact with the target nerve tissue of the patient directly. The quantity of the leads 12 can be selected according to need, such as one or more. The wire 13 is configured to connect the pulse generator 11 to the leader 12. The wire 13 is optional. In one embodiment, the lead 12 is electrically connected to the pulse generator 11 directly.

Figure 2:
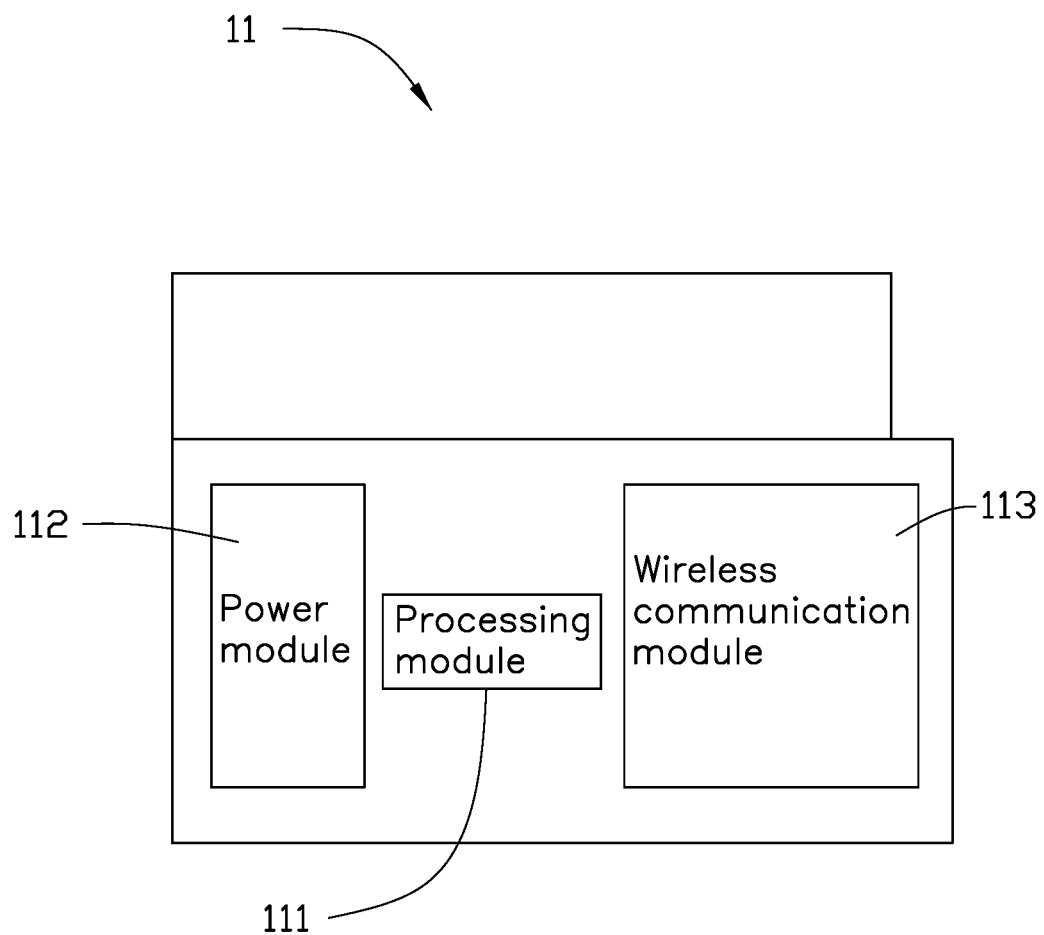
FIG. 2 is a schematic view of one embodiment of a pulse generator of the implantable medical device of FIG. 1.

As shown in FIG. 2, the pulse generator 11 includes a processing module 111, a power module 112 and a wireless communication module 113. The processing module 111, the power module 112 and the wireless communication module 113 are electrically connected to each other. The processing module 111 has stored program and can generate the electrical stimulation pulses 15 at different frequencies, with different pulse widths, or at different amplitudes. The waveform of the electrical stimulation pulses 15 are not limited and can be any kinds of waveform, such as triangle wave, rectangle wave or sinusoidal wave. The wireless communication module 113 is configured to communicate with the programmer 14 wirelessly so that the program of the processing module 111 can be selected and adjusted by the programmer 14. Thus, the electrical stimulation pulses 15 delivered from the pulse generator 11 can be changed by the programmer 14.

Figure 3:
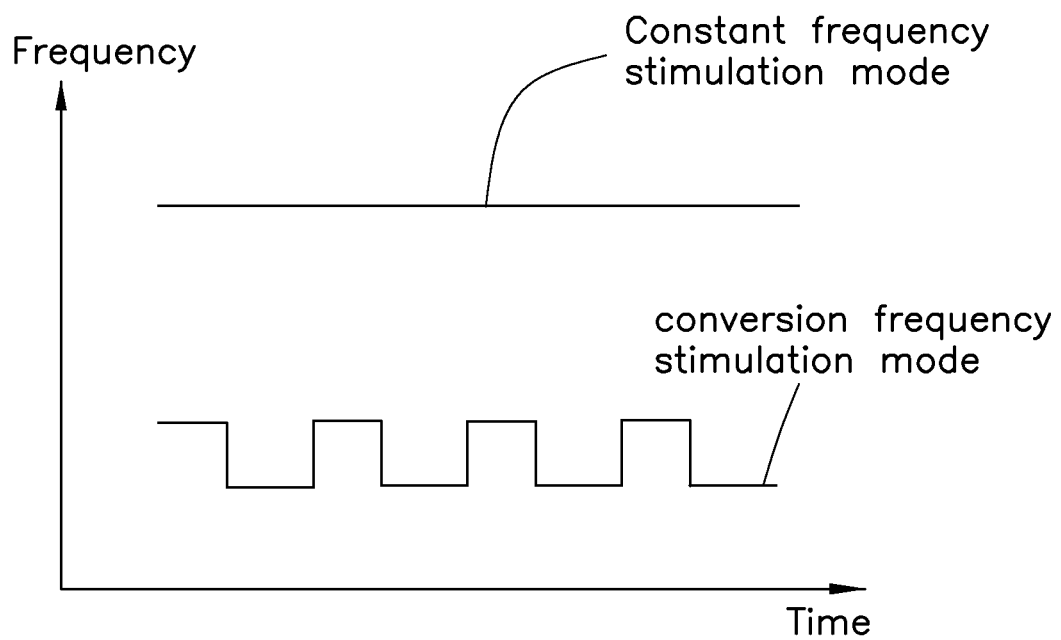
FIG. 3 shows relationships of frequency-to-time of a constant frequency stimulation mode and a variable frequency stimulation mode of one embodiment.

As shown in FIG. 3, the pulse generator 11 has a constant frequency stimulation mode configured to generate a constant frequency stimulation pulse and a variable frequency stimulation mode configured to generate a variable frequency stimulation pulse. In this case, the pulse generator 11 has at least the variable frequency stimulation mode to generate the variable frequency stimulation pulse. In one embodiment, the processing module 111 comprises a constant frequency stimulation module configured to achieve the constant frequency stimulation mode and a variable frequency stimulation module configured to achieve the variable frequency stimulation mode. The constant frequency stimulation module and the variable frequency stimulation module can be the same integrated circuit (IC) or two different integrated circuits.

Figure 4:
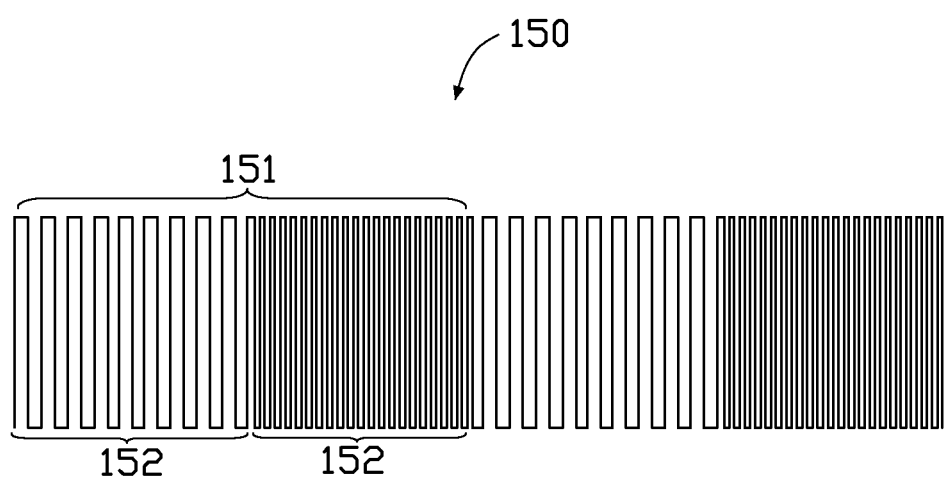
FIG. 4 is a schematic view of one embodiment of a first kind of variable frequency stimulation pulse.
Figure 5:
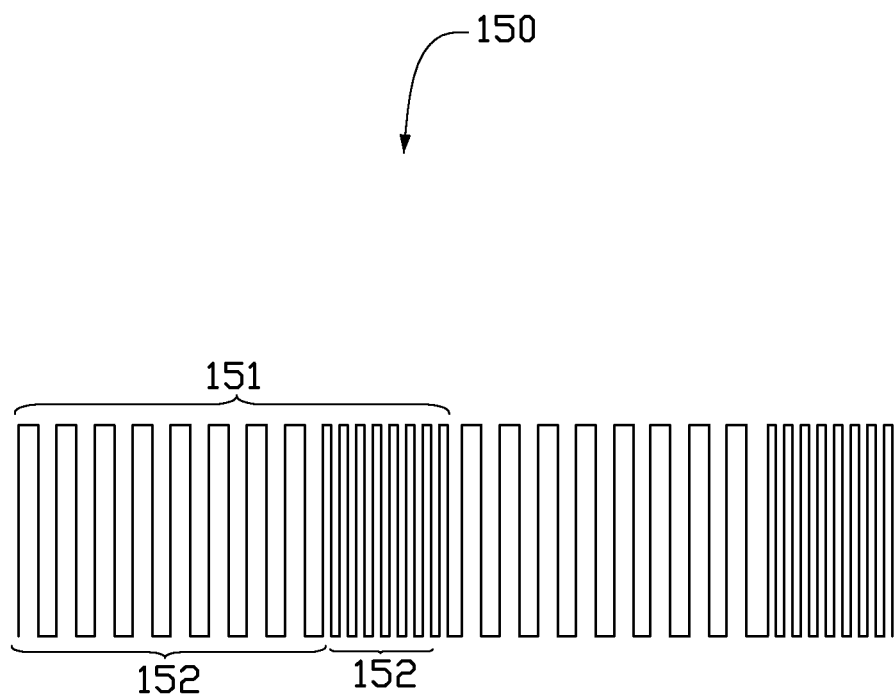
FIG. 5 is a schematic view of one embodiment of a second kind of variable frequency stimulation pulse.
Figure 6:
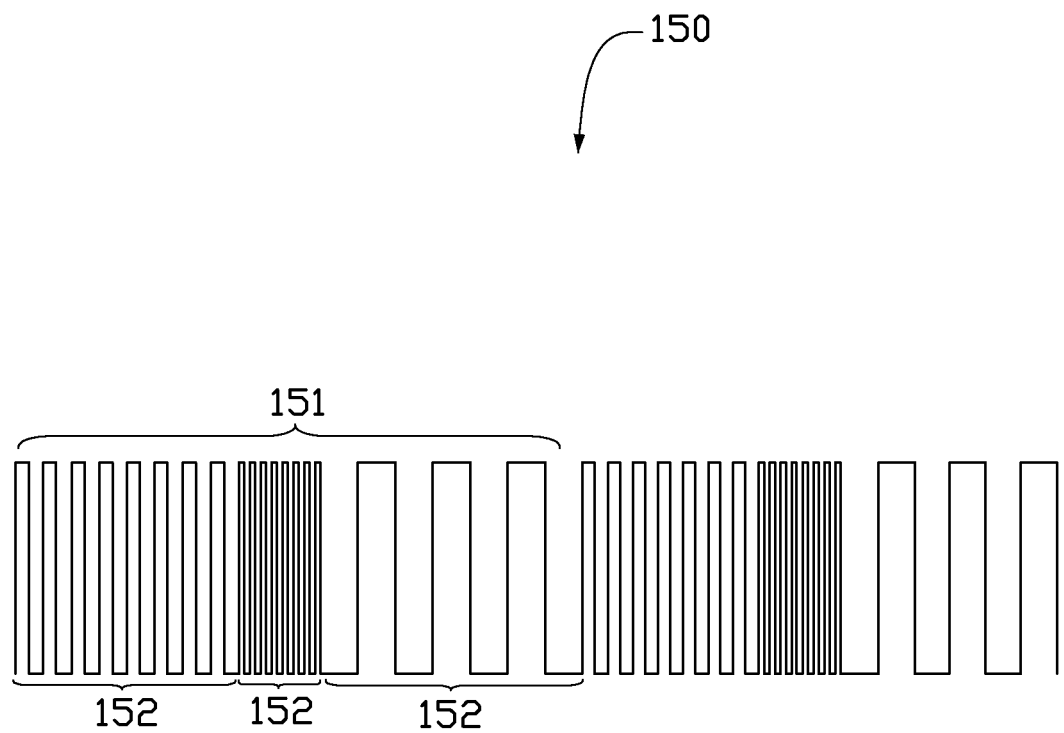
FIG. 6 is a schematic view of one embodiment of a third kind of variable frequency stimulation pulse.

As shown in FIGS. 4-6, the variable frequency stimulation pulse 150 includes at least two alternate electrical stimulation pulse trains 152 at different frequencies to form a plurality of pulse train periods 151. The at least two electrical stimulation pulse trains 152 can alternately stimulate the target nerve tissue. In each pulse train period 151, the electrical stimulation pulse train 152 has a duration in a range from about 0.1 seconds to about 60 minutes. If the duration of the electrical stimulation pulse train 152 is too short, for example, less than 0.1 seconds, the stimulation time of the electrical stimulation pulse train 152 and the pulse width of a single pulse would merge and be indistinguishable. Thus, different electrical stimulation pulse trains 152 would follow each other too closely, and the treatment effect would be uncontrolled. If the duration of the electrical stimulation pulse train 152 is too long, for example, more than 60 minutes, the patient would adapt to the electrical stimulation of a certain single frequency over a long time, just like the constant frequency stimulation mode.

In one embodiment, the electrical stimulation pulse train 152 in each pulse train period 151 has a duration in a range from about 0.1 seconds to about 30 minutes. In one embodiment, the electrical stimulation pulse train 152 in each pulse train period 151 has a duration in a range from about 3 seconds to about 60 seconds. In another embodiment, the electrical stimulation pulse train 152 in each pulse train period 151 has a duration in a range from about 5 seconds to about 30 seconds. In the range from about 5 seconds to about 30 seconds, not only does the electrical stimulation pulse train 152 of each single frequency stimulate the target nerve tissue for an effective amount of time, but also it can prevent the patients from adapting.

The frequency of the electrical stimulation pulse train 152 should be less than 400 Hz. In one embodiment, the frequency of the electrical stimulation pulse train 152 can be in a range from about 30 Hz to about 250 Hz. In another embodiment, the frequency of the electrical stimulation pulse train 152 can be in a range from about 50 Hz to about 150 Hz. When the frequency is less than 10 Hz, improvement in the motor symptoms are not obvious, the motor symptoms may even deteriorate at a too low frequency. Clinical trials show that the frequency about 100 Hz has better treatment effect. Therefore, in the range from about 50 Hz to about 150 Hz, it can not only improve the motor symptoms, but also discourage the non-motor symptoms.

The arithmetic mean frequency of the at least two electrical stimulation pulse trains 152 can be in the range from about 60 Hz to about 180 Hz. In one embodiment, the arithmetic mean frequency can be in the range from about 80 Hz to about 120 Hz. The geometrical mean frequency of the at least two electrical stimulation pulse trains 152 can also be in the range from about 60 Hz to about 180 Hz. In one embodiment, the geometrical mean frequency can be in the range from about 80 Hz to about 120 Hz.

Clinical trials show that the electrical stimulation therapy at high frequency from about 90 Hz to about 400 Hz can improve the motor symptoms of Parkinson patients, and the electrical stimulation therapy at from about 10 Hz to about 90 Hz can depress and discourage some non-motor symptoms, such as dysarthria, dyskinesia or freezing of gait. When the variable frequency stimulation pulse 150 includes two alternate electrical stimulation pulse trains 152, one electrical stimulation pulse train 152 can have a first frequency from about 50 Hz to about 80 Hz and the other one electrical stimulation pulse trains 152 can have a second frequency from about 100 Hz to about 150 Hz.

The quantity of the at least two electrical stimulation pulse trains 152 is N, wherein N≥2. In one embodiment, 2≤N≤10. In one embodiment, 2≤N≤5. In another embodiment, N=2 or 3. If there are too many electrical stimulation pulse trains 152, adjusting the parameters of the variable frequency stimulation pulse 150 is too complicated. The quantity of the at least two electrical stimulation pulse trains 152 can be increased gradually and optimized for the best treatment effect.

The time ratio of each electrical stimulation pulse train 152 in each pulse train period 151 is greater than 5%. In one embodiment, the time ratio is greater than 20%. In another embodiment, the time ratio is greater than 30%. In another embodiment, the time ratio is about 1/N, wherein N is the quantity of the at least two electrical stimulation pulse trains 152. For example, when N=2, the time ratio is about 50%. When the time ratio is above 5%, the electrical stimulation pulse train 152 has a significant therapeutic treatment effect on a certain symptom.

The order of the at least two electrical stimulation pulse trains 152 in each pulse train period 151 can be from high frequency to low frequency, from low frequency to high frequency, or at random as long as each electrical stimulation pulse train 152 has a certain time ratio in each pulse train period 151.

The electrical stimulation pulse train 152 can be current mode or voltage mode. In current mode, the current can be in a range from about 0 mA to about 30 mA with a regulated precision of 0.1 mA. When in voltage mode, the voltage can be in a range from about 0 V to about 15 V with a regulated precision of 0.1 V. In one embodiment, the amplitude of the variable frequency stimulation pulse is variable so that the charge can be modulated by changing the amplitude. The amplitude can be adjusted in a range from about 0 V to about 10 V with a regulated precision of 0.1 mV at a voltage mode; or the amplitude can be adjusted in a range from about 0 mA to about 10 mA with a regulated precision of 0.1 mA at a current mode. Usually, the amplitude can be adjusted in a range from about 0 V to about 5 V or in a range from about 0 mA to about 5 mA. In one embodiment, the pulse width of the variable frequency stimulation pulse is variable so that the charge can be modulated by changing pulse width. The pulse width can be adjusted in a range from about 0 μs to about 1000 μs with a regulated precision of 1 μs at a voltage mode. Usually, the pulse width can be adjusted in a range from about 0 μs to about 150 μs.

As shown in FIG. 4, in one embodiment, the first kind of variable frequency stimulation pulse 150 includes two alternate electrical stimulation pulse trains 152 at different frequencies to form a plurality of pulse train periods 151, and the two electrical stimulation pulse trains 152 have the same time ratio. As shown in FIG. 5, in one embodiment, the second kind of variable frequency stimulation pulse 150 includes two alternate electrical stimulation pulse trains 152 at different frequencies to form a plurality of pulse train periods 151, and the two electrical stimulation pulse trains 152 have different time ratios. As shown in FIG. 6, in one embodiment, the third kind of variable frequency stimulation pulse 150 includes three alternate or cyclic electrical stimulation pulse trains 152 at different frequencies to form a plurality of pulse train periods 151, and the three electrical stimulation pulse trains 152 have different time ratios.

Figure 7:
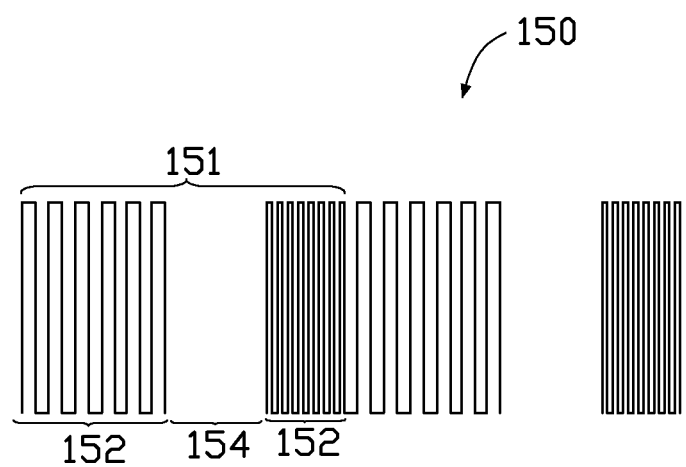
FIG. 7 is a schematic view of one embodiment of a fourth kind of variable frequency stimulation pulse.
Figure 8:
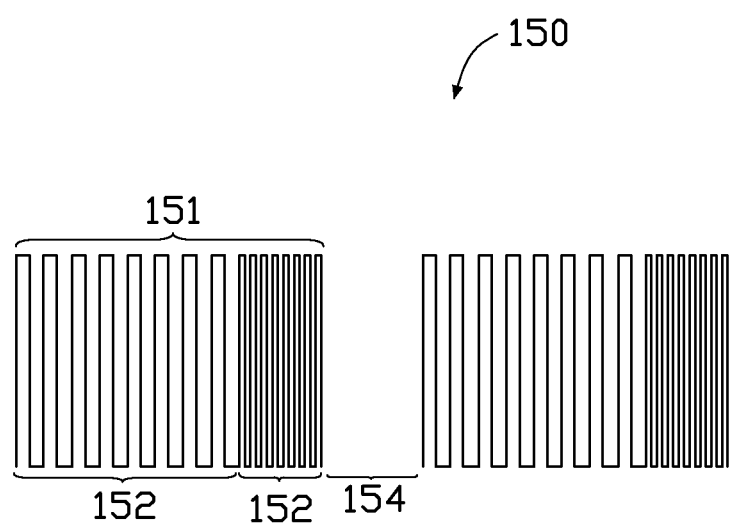
FIG. 8 is a schematic view of one embodiment of a fifth kind of variable frequency stimulation pulse.

As shown in FIG. 7, in one embodiment of the fourth kind of variable frequency stimulation pulse 150, the plurality of electrical stimulation pulse trains 152 can be continuous or non-continuous. There can be a time space 154 between adjacent two electrical stimulation pulse trains 152. As shown in FIG. 8, in one embodiment of the fifth kind of variable frequency stimulation pulse 150, the plurality of pulse train periods 151 can be continuous or non-continuous. There can be a time space 154 between adjacent two pulse train periods 151. The time space 154 can be in a range from about 0.01 seconds to about 60 minutes. In one embodiment, the time space 154 can be in a range from about 0.01 seconds to about 60 seconds. In one embodiment, the time space 154 is T/N, wherein T is the time length of the pulse train period 151, and N is the quantity of the at least two electrical stimulation pulse trains 152. Therefore, the time space 154 should not be so long that the stimulation has no effect.

Furthermore, the pulse generator 11 can store a plurality of experiential stimulation frequencies combinations, such as "50 Hz and 150 Hz", "60 Hz and 140 Hz", "70 Hz and 130 Hz", "80 Hz and 120 Hz", or "90 Hz and 110 Hz". The two different experiential stimulation frequencies of each combination have the same arithmetic mean frequency. In operation, the two electrical stimulation pulse trains 152 can have the two different experiential stimulation frequencies with each having a time ratio of 50%. Furthermore, the pulse generator 11 can store a plurality of experiential stimulation currents, such as 0.5 mA, 1 mA, 1.5 mA, 2 mA, or 2.5 mA. The experiential stimulation currents and the experiential stimulation frequencies can be selected according to need. For example, in general working state, the experiential stimulation frequencies of 80 Hz and 120 Hz and the experiential stimulation current of 2 mA can be used, wherein each of the 80 Hz and 120 Hz frequencies has a time ratio of 50%. For example, for the less-affected patients, the experiential stimulation frequencies of 80 Hz and 120 Hz and the experiential stimulation current of 1.5 mA can be used, wherein each of the 80 Hz and 120 Hz frequencies has a time ratio of 50%.

Furthermore, the pulse generator 11 can have a frequency scan function. When the parameters of the frequency scan are set, the pulse generator 11 can scan in a frequency range according to the frequency scan modes.

Figure 9:
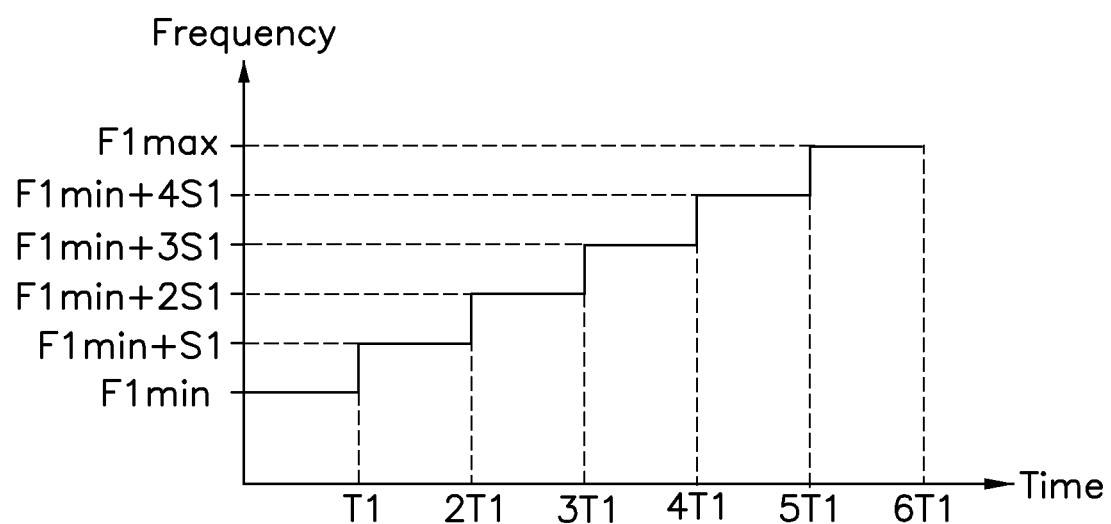
FIG. 9 shows a relationship of frequency-to-time in one embodiment of a first kind of frequency scan mode.

In one embodiment, the first kind of frequency scan mode is called single-frequency scan. In the single-frequency scan mode, the frequency scan range can be set as F1min~F1max, the scan precision can be set as S1, and the scan time can be set as T1. Here, the pulse generator 11 would generate a plurality of constant frequency stimulation pulses one by one at the frequencies of F1min, F1min+S1, F1min+2S1, F1min+3S1 . . . F1min+nS1 and F1max, wherein n is natural number and satisfies the formula: n≤(F1max−F1min)/S1. Each of the plurality of constant frequency stimulation pulses has a duration of T1. The scan range F1min~F1max can be in a range from 0 Hz to 400 Hz. The scan precision S1 can be in a range from 1 Hz to 10 Hz, such as from 2 Hz to 5 Hz. The scan time T1 can be in a range from 5 seconds to 60 minutes, such as from 10 seconds to 30 minutes. For example, the frequency scan range is from 50 Hz to 150 Hz, the scan precision is 10 Hz, and the scan time is 10 seconds. The pulse generator 11 would generate a plurality of constant frequency stimulation pulses one by one at the frequencies of 50 Hz, 60 Hz, 70 Hz, 80 Hz, 90 Hz, 100 Hz, 110 Hz, 120 Hz, 130 Hz, 140 Hz and 150 Hz. Each of the plurality of constant frequency stimulation pulses has a duration of 10 seconds. FIG. 9 shows a relationship of frequency-to-time in one embodiment of a first kind of frequency scan mode, wherein n=4.

Figure 10:
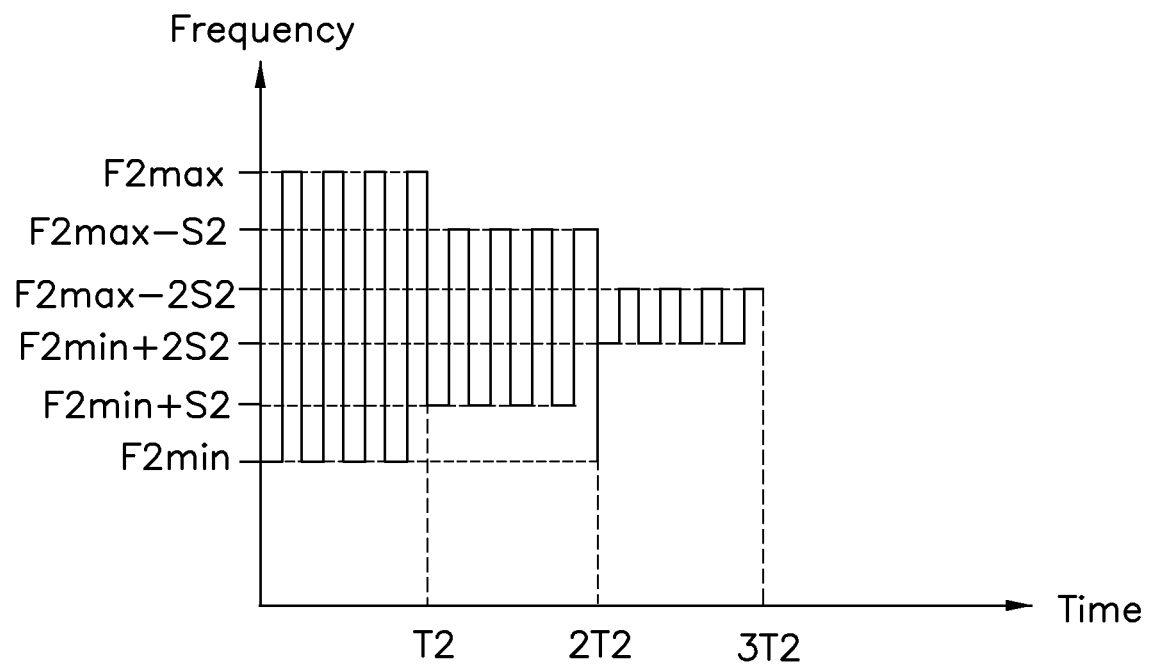
FIG. 10 shows a relationship of frequency-to-time in one embodiment of a second kind of frequency scan mode.

In one embodiment, the second kind of frequency scan mode is called multi-frequency alternating closing scan. In the multi-frequency alternately closing scan mode, the frequency scan range can be set as F2min~F2max, the scan precision can be set as S2, and the scan time can be set as T2. Here, the pulse generator 11 would generate a plurality variable frequency stimulation pulses 150 one by one at the frequency combinations of "F2min and F2max", "F2min+S2 and F2max−S2", "F2min+2S2 and F2max−2S2" . . . and "F2min+nS2 and F2max−nS2", wherein n is natural number and satisfies the formula: n<(F2max−F2min)/2S2. Each of the plurality variable frequency stimulation pulses 150 has an entire duration of T2. The scan time T2 should be integer times the duration of each pulse train period 151. Each of the plurality variable frequency stimulation pulses 150 includes two alternate electrical stimulation pulse trains 152. The scan range F2min~F2max can be in a range from 0 Hz to 400 Hz. The scan precision S2 can be in a range from 1 Hz to 10 Hz, such as from 2 Hz to 5 Hz. The scan time T2 can be in a range from 5 seconds to 60 minutes, such as from 30 seconds to 10 minutes. For example, the frequency scan range is from 50 Hz to 150 Hz, the scan precision S2 is 10 Hz, and the scan time T2 is 30 seconds, the duration of the pulse train period 151 is 2 seconds, and the duration of each electrical stimulation pulse train 152 is 1 second. The pulse generator 11 would generate a plurality variable frequency stimulation pulses 150 one by one at the frequency combinations of "50 Hz and 150 Hz", "60 Hz and 140 Hz", "70 Hz and 130 Hz", "80 Hz and 120 Hz", and "90 Hz and 110 Hz". FIG. 10 shows a relationship of frequency-to-time in one embodiment of a second kind of frequency scan mode, wherein n=2.

Figure 11:
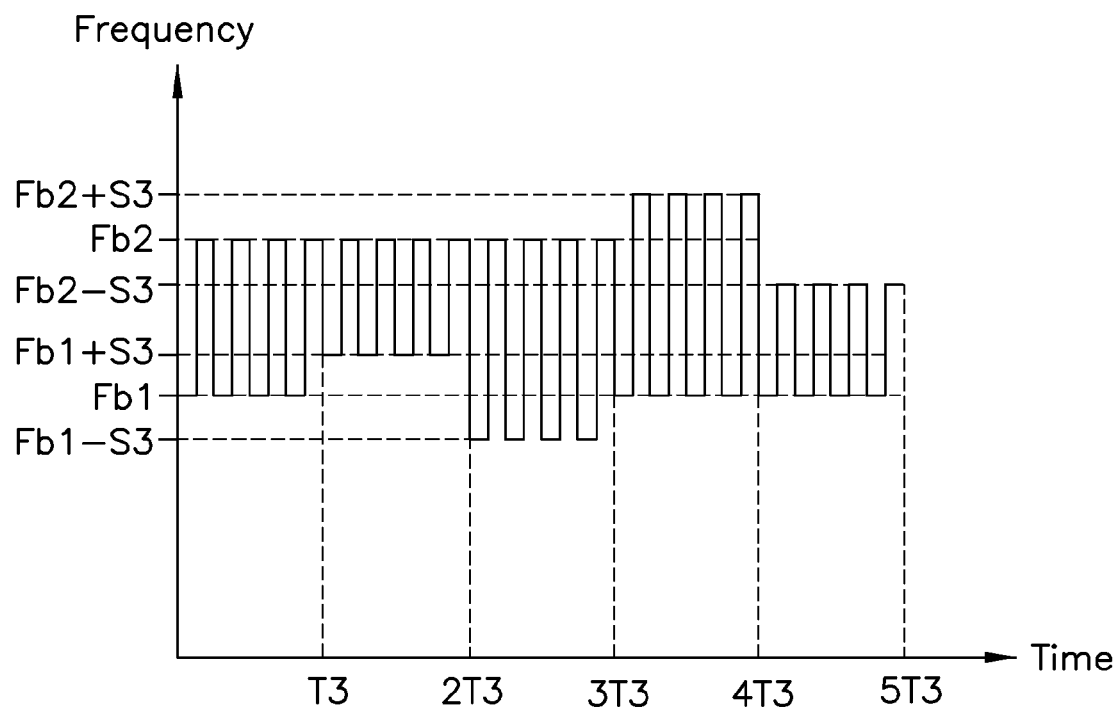
FIG. 11 shows a relationship of frequency-to-time in one embodiment of a third kind of frequency scan mode.

In one embodiment, the third kind of frequency scan mode is called multi-frequency alternating combining scan. In the multi-frequency alternately combining scan mode, the base frequencies can be set as Fb1 and Fb2, the scan range can be set as F3, the scan precision can be set as S3, and the scan time can be set as T3. Here, the pulse generator 11 would generate a plurality variable frequency stimulation pulses 150 one by one at the frequency combinations of "Fb1 and Fb2", "Fb1+S3 and Fb2", "Fb1+2S3 and Fb2" . . . "Fb1+nS3 and Fb2", "Fb1–S3 and Fb2", "Fb1–2S3 and Fb2" . . . "Fb1–nS3 and Fb2", "Fb1 and Fb2+S3", "Fb1 and Fb2+2S3" . . . "Fb1 and Fb2+nS3", "Fb1 and Fb2–S3", "Fb1 and Fb2–2S3" . . . and "Fb1 and Fb2–nS3", wherein n is natural number and satisfies the formula: n=F3/S3. Each of the plurality variable frequency stimulation pulses 150 has an entire duration of T3. The scan time T3 should be integer times the duration of each pulse train period 151. The scan range F3 should be integer times the scan precision S3. Each of the plurality variable frequency stimulation pulses 150 includes two alternate electrical stimulation pulse trains 152. The base frequencies Fb1 and Fb2 can be selected according to need and usually in a range from 60 Hz to 120 Hz. The scan range F3 can be in a range from 1 Hz to 20 Hz, such as from 5 Hz to 10 Hz. The scan precision S3 can be in a range from 1 Hz to 10 Hz, such as from 2 Hz to 5 Hz. The scan time T3 can be in a range from 5 seconds to 60 minutes, such as from 30 seconds to 10 minutes. For example, the base frequencies Fb1 are set as 80 Hz and 100 Hz, the frequency scan range F3 is 10 Hz, the scan precision S3 is 5 Hz, and the scan time T3 is 60 seconds, the duration of each pulse train period 151 is 3 seconds, the duration of one of the two electrical stimulation pulse trains 152 is 1 second, and the duration of the other one of the two electrical stimulation pulse trains 152 is 2 seconds. The pulse generator 11 would generate a plurality variable frequency stimulation pulses 150 one by one at the frequency combinations of "80 Hz and 100 Hz", "85 Hz and 100 Hz", "90 Hz and 100 Hz", "75 Hz and 100 Hz", "70 Hz and 100 Hz", "80 Hz and 105 Hz", "80 Hz and 110 Hz", "80 Hz and 95 Hz" and "80 Hz and 90 Hz". FIG. 11 shows a relationship of frequency-to-time in one embodiment of a second kind of frequency scan mode, wherein F3=S3.

In one embodiment, the fourth kind of frequency scan mode is also called multi-frequency alternating combining scan. In the multi-frequency alternating combining scan mode, the base frequencies can be set as Fb1 and Fb2, the scan range can be set as F3, the scan precision can be set as S3, and the scan time can be set as T3. Here, the pulse generator 11 would generate a plurality variable frequency stimulation pulses 150 one by one at the frequency combinations of "Fb1 and Fb2", "Fb1+S3 and Fb2+S3", "Fb1+2S3 and Fb2+2S3" . . . "Fb1+nS3 and Fb2+nS3", "Fb1–S3 and Fb2–S3", "Fb1–2S3 and Fb2–2S3" . . . "Fb1–nS3 and Fb2–nS3", "Fb1+S3 and Fb2–S3", "Fb1+2S3 and Fb2–2S3" . . . "Fb1+nS3 and Fb2–nS3", "Fb1–S3 and Fb2+S3", "Fb1–2S3 and Fb2+2S3", . . . and "Fb1–nS3 and Fb2+nS3", wherein n is natural number and satisfies the formula: n=F3/S3.

Figure 12:
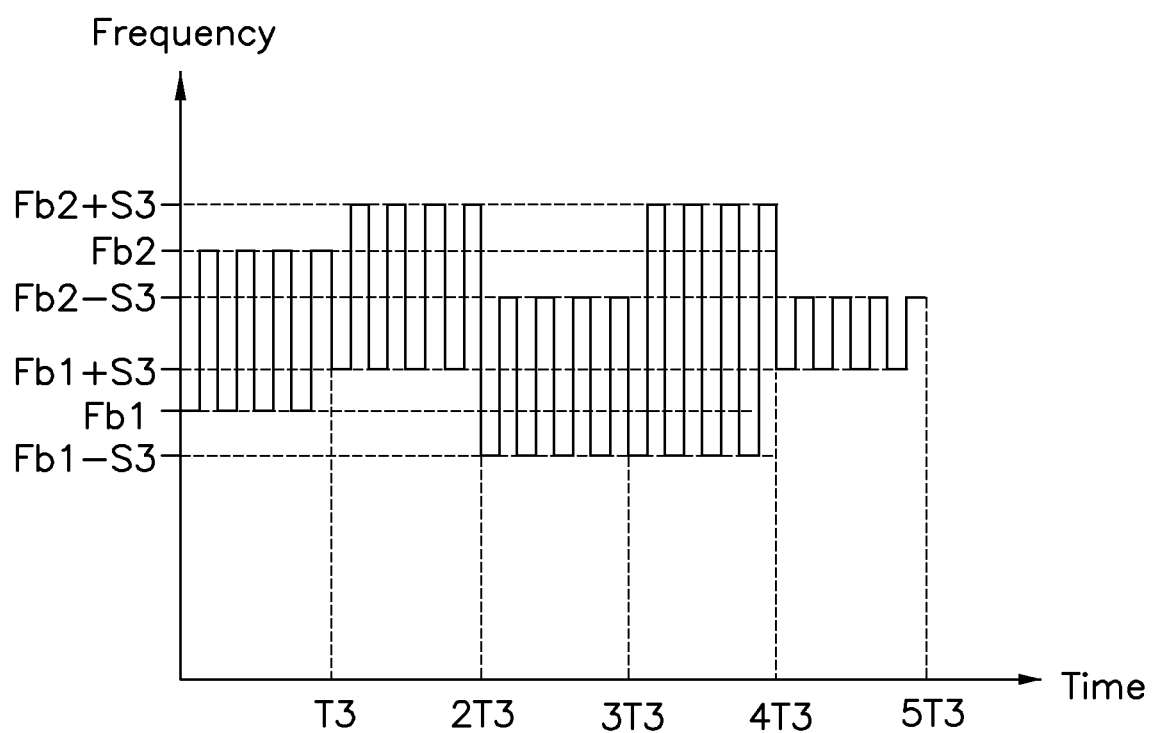
FIG. 12 shows a relationship of frequency-to-time in one embodiment of a fourth kind of frequency scan mode.

The fourth kind of frequency scan mode is similar to the third kind of frequency scan mode as above except that in the third kind of frequency scan mode, only one of the Fb1 and Fb2 is variable, however, in the fourth kind of frequency scan mode, both the Fb1 and Fb2 are variable. For example, the base frequencies Fb1 are set as 80 Hz and 105 Hz, the frequency scan range F3 is 10 Hz, the scan precision S3 is 5 Hz, and the scan time T3 is 60 seconds, the duration of each pulse train period 151 is 3 seconds, the duration of one of the two electrical stimulation pulse trains 152 is 1 second, and the duration of the other one of the two electrical stimulation pulse trains 152 is 2 seconds. The pulse generator 11 would generate a plurality variable frequency stimulation pulses 150 one by one at the frequency combinations of "80 Hz and 105 Hz", "85 Hz and 110 Hz", "90 Hz and 115 Hz", "75 Hz and 100 Hz", "70 Hz and 95 Hz", "85 Hz and 100 Hz", "90 Hz and 95 Hz", "75 Hz and 110 Hz" and "70 Hz and 115 Hz". FIG. 12 shows a relationship of frequency-to-time in one embodiment of a second kind of frequency scan mode, wherein F3=S3.

Figure 13:
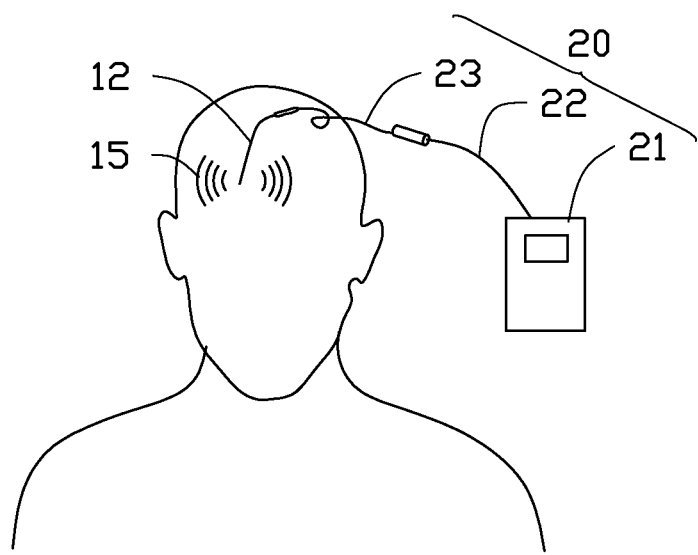
FIG. 13 is a schematic view of one embodiment of an electrical stimulation testing device.

As shown in FIG. 13, the electrical stimulation testing device 20 of one embodiment usually includes programmer 21, a cable 22, a wire 23, and a lead 12.

In use, the lead 12 is implanted in body of patient. One end of the wire 23 is electrically connected to the programmer 21 through the cable 22, and the other end of the wire 23 is electrically connected to the lead 12. The programmer 21 is configured to generate electrical stimulation pulses 15 and deliver the electrical stimulation pulses 15 to the lead 12. If the electrical stimulation treatment is appropriate for the patient, the leader 12 is kept in the body of the patient and does not need to be removed.

The cable 22 is optional. In one embodiment, the wire 23 is electrically connected to the programmer 21 directly. The cable 22 does not have to be made of biocompatible materials. The wire 23 includes a connector on each end. Because part of the wire 23 would in the body, at least part of the wire 23 should be made of biocompatible materials. The entire wire 23 can be made of biocompatible materials.

Figure 14:
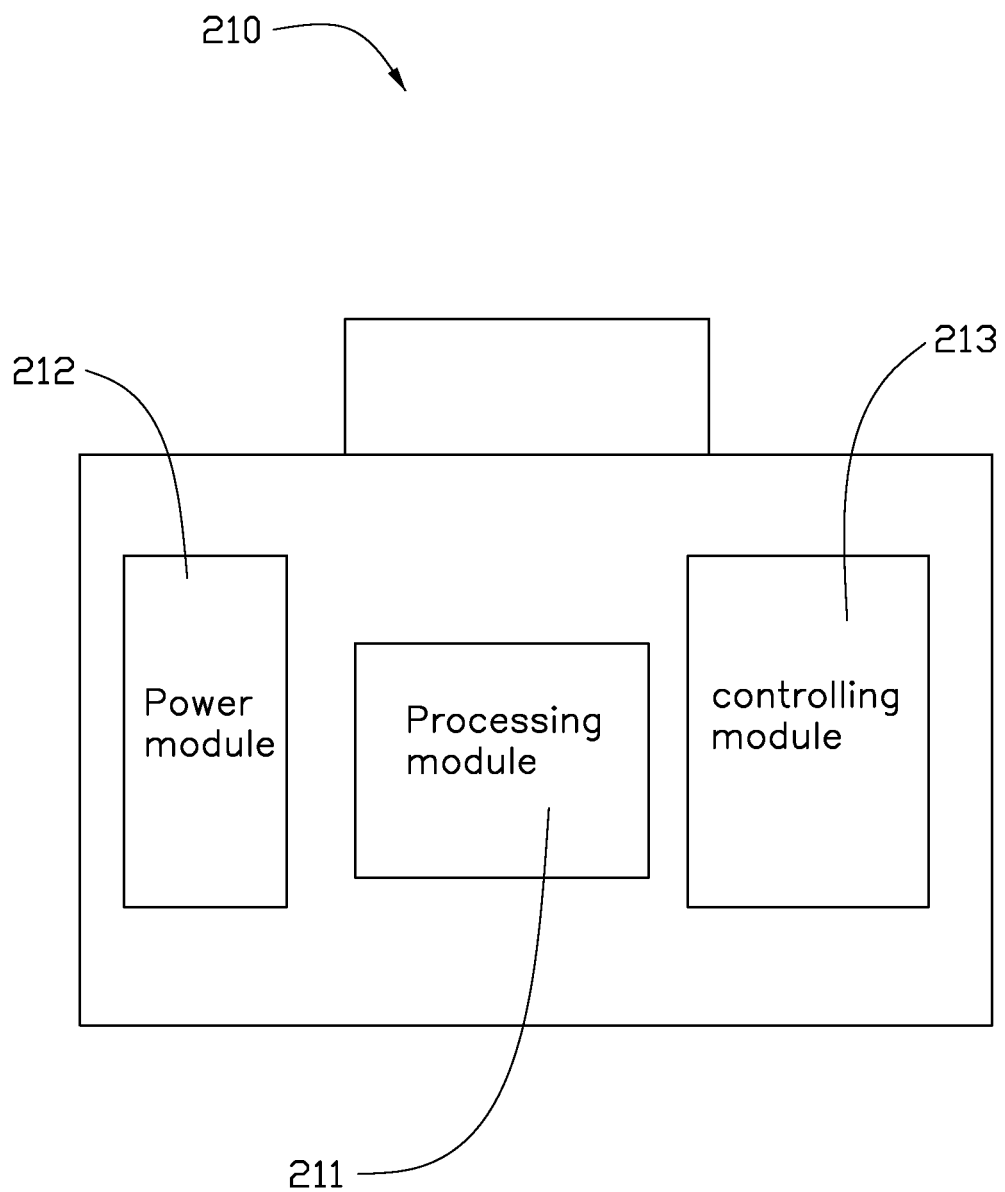
FIG. 14 is a schematic view of one embodiment of a pulse generator of the electrical stimulation testing device of FIG. 13.

As shown in FIG. 14, the programmer 21 includes a pulse generator 210. The pulse generator 210 includes a processing module 211, a power module 212 and a controlling module 213. The processing module 211, the power module 212 and the controlling module 213 are electrically connected to each other. The processing module 211 has compiled programs and can generate the electrical stimulation pulses 15 at different frequencies, with different pulse widths, or at different amplitudes. The controlling module 213 includes a display screen, a keyboard, and so on. The controlling module 213 is configured to select and adjust the program of the processing module 211. The pulse generator 210 does not have to be made of biocompatible materials.

As shown in FIGS. 3-8, the pulse generator 210 has at least the variable frequency stimulation mode to generate variable frequency stimulation pulse 150 above. As shown in FIGS. 9-12, the pulse generator 210 can have a frequency scan function of the pulse generator 11 above.

Furthermore, an electrical stimulation therapy method is provided. The electrical stimulation therapy method includes following steps:

step (S10), implanting the lead 12 in a brain of the patient so that at least one stimulation contactor of the lead 12 contact with target nerve tissue of the patient directly;

step (S20), coupling the lead 12 to the pulse generator 11;

step (S30), determining the stimulation frequencies of the variable frequency stimulation pulse 150; and step (S40), applying the variable frequency stimulation pulse 150 to the target nerve tissue.

In step (S10), the lead 12 is implanted in brain of the Parkinson patient. In step (S30), the pulse generator 11 is implanted in body of the Parkinson patient and electrically connected to the lead 12 by wire 13.

In step (S30), the stimulation frequencies of the variable frequency stimulation pulse 150 can be determined by different methods.

In one embodiment, the first method is for the first kind of patient who had been treated by the constant frequency stimulation pulse for a long time and still has some non-motor symptoms. The normal frequency of the constant frequency stimulation pulse for the first kind of patient is recorded as A. Usually, the normal frequency of the constant frequency stimulation pulse for the one of the first kind of patient is deterministic value. Then, the first kind of patient is applied with different constant frequency stimulation pulses until one of the non-motor symptoms is discouraged. The frequency of the constant frequency stimulation pulse on which the one of the non-motor symptoms is discouraged is recorded as B. A frequency C is calculated by the formula $C=A^2/B$. The geometrical mean frequency of frequency C and frequency B is the frequency A. The frequency B and frequencies C are used as the stimulation frequencies of the variable frequency stimulation pulse 150.

If the first kind of patient has two non-motor symptoms, the frequencies of the constant frequency stimulation pulse on which the two non-motor symptoms are discouraged are recorded as B1 and B2. Frequencies C and D can be calculated by the formula $C=A^2/B1$ and $D=A^2/B2$. Thus, the frequency B, frequency C and frequency D are used as the stimulation frequencies of the variable frequency stimulation pulse 150. The frequency C can also be calculated by the formula C=2A−B. The arithmetic mean frequency of the frequency C and frequency B is the frequency A. If the first kind of patient has two non-motor symptoms, frequencies C and D can be calculated by the formula C=2A−B1 and D=2A−B2.

In another embodiment, the second method is for the second kind of patient who is the first time to be treated by electrical stimulation therapy. If the second kind of patient has two symptoms, applying constant frequency stimulation pulses at different frequencies one by one to stimulate the target nerve tissue by using the single-frequency scan mode; and the frequencies of the constant frequency stimulation pulses on which two symptoms are alleviated are recorded as B1 and B2. The frequency B1 and frequency B2 are used as the stimulation frequencies of the variable frequency stimulation pulse 150. It only takes about ten seconds to about several minutes to find the frequencies of the constant frequency stimulation pulses on which two symptoms are alleviated or improved. If the second kind of patient has more than two symptoms, the frequencies of the constant frequency stimulation pulses on which the symptoms are alleviated or improved can be recorded as B1, B2, B3, . . . Bn.

Furthermore, a step of frequency scanning can be performed at the multi-frequency alternately combining scan mode so that to find better stimulation frequencies of the variable frequency stimulation pulse 150, wherein the frequencies "B and C" or frequencies "B1 and B2" are used as the base frequencies in the step of frequency scanning.

In step (S40), the applying the variable frequency stimulation pulse 150 to the target nerve tissue further includes adjusting the parameters of the variable frequency stimulation pulse 150 to achieve the best treatment effect.

For example, the time ratio of the electrical stimulation pulse train 152 can be set as 1/N, wherein N is the quantity of the electrical stimulation pulse trains 152 at first. If one symptom is not obviously improved, the time ratio of the electrical stimulation pulse train 152 corresponding to the symptom can be increased so that all symptoms are improved at balance.

For example, the amplitude of the variable frequency stimulation pulse can be adjusted so that the stimulation charge can be constant. The at least two electrical stimulation pulse trains 152 can have different amplitudes. The amplitude can be adjusted in a range from about 0 V to about 10 V with a regulated precision of 0.1 mV at a voltage mode; or the amplitude can be adjusted in a range from about 0 mA to about 10 mA with a regulated precision of 0.1 mA at a current mode. Usually, the amplitude can be adjusted in a range from about 0 V to about 5 V or in a range from about 0 mA to about 5 mA.

For example, the pulse width of the variable frequency stimulation pulse can be adjusted so that the stimulation charge can be constant. The at least two electrical stimulation pulse trains 152 can have different pulse widths. The pulse width can be adjusted in a range from about 0 µs to about 1000 µs with a regulated precision of 1 µs at a voltage mode. Usually, the pulse width can be adjusted in a range from about 0 us to about 150 µs.

For example, the stimulation frequencies of the variable frequency stimulation pulse 150 can be optimized to achieve the best treatment effect. The stimulation frequencies of the variable frequency stimulation pulse 150 can be optimized through the frequency scan functions of the pulse generator 11.

Usually, the constant frequency stimulation mode of prior art would cause some non-motor symptoms and result in adaptability at the time of improving the motor symptoms. In this case, it can discourage or even eliminate the non-motor symptoms and avoid the adaptability on the condition of improving the motor symptoms by applying variable frequency stimulation pulses 150 at variable frequency stimulation mode.

For example, to Parkinson patients, the deep brain stimulation on the subthalamic nucleus at constant frequency stimulation mode would obviously improve the motor symptoms, such as tremors and rigidity. However, the stimulation on the subthalamic nucleus at constant frequency stimulation mode would cause some non-motor symptoms, such as dysarthria or freezing of gait. Also, for the stimulation at constant frequency stimulation mode, such as 100 Hz, it is easy for the patients to be adaptable, which is like resistance to the action of a drug and will cause bad treatment effect.

In some clinical cases, the variable frequency stimulation mode had been used to treat the patients, such as Parkinson disease. Clinical cases shows that the electrical stimulation therapy method of variable frequency stimulation can overcome the non-motor symptoms, such as freezing of gait, dysarthria or dyskinesia, and avoid the adaptabilities which are caused by constant frequency stimulation mode on the condition of improving the motor symptoms, such as tremors and/or rigidity. Also, clinical cases shows that the variable frequency stimulation therapy method is benefit for other nerve diseases related to movement, such as dystonia, and nerve diseases related to cognitive and psychology, such as depression, habituation.

Case 1

Parkinson patient X had been treated for a long time by the constant frequency stimulation mode at 130 Hz and has some non-motor symptoms of dysarthria. The normal frequency A of the Parkinson patient is 130 Hz.

It is found that the dysarthria can be improved at the frequency B of 60 Hz by using the single-frequency scan mode to apply constant frequency stimulation pulses at different frequencies to the target nerve tissue one by one.

Parkinson patient X is treated by a variable frequency stimulation pulses including a first frequency 60 Hz and a second frequency 130 Hz, wherein the electrical stimulation pulse trains at the first frequency or the second frequency has a time ratio of 50% and a duration of 10 seconds. Then, it is found that the improvement is better at the first frequency 60 Hz and the second frequency 130 Hz are adjusted after fine adjustment. After treating by the variable frequency stimulation pulses, the dysarthria is improved obviously on the condition of improving the motor symptoms of tremors. Table 1 is a comparison of vocal efficiency between constant frequency stimulation and variable frequency stimulation.

TABLE 1

Comparison of voicing efficiency

| Voicing efficiency parameters | Normal range | 130 Hz constant frequency | 60 Hz&130 Hz variable frequency |
|---|---|---|---|
| Peak air pressure (cmH$_2$O) | 6.65 ± 1.96 | 36.23 | 3.9 |
| Mean peak air pressure (cmH$_2$O) | 5.57 ± 1.72 | 22.42 | 3.79 |
| Peak expiratory airflow (Lit/Sec) | 0.19 ± 0.10 | 3.41 | 0.78 |
| Target airflow (Lit/Sec) | 0.11 ± 0.05 | 1.25 | 0.16 |
| Expiratory Volume (Liters) | 0.17 ± 0.12 | 1.72 | 0.13 |
| Mean airflow during voicing (Lit/Sec) | 0.11 ± 0.05 | 1.27 | 0.12 |
| Aerodynamic Power (watts) | 0.060 ± 0.040 | 2.743 | 0.060 |
| Aerodynamic resistance cmH$_2$O/(l/s) | 55.18 ± 30.64 | 17.62 | 23.03 |

Case 2

Parkinson patient Y has the symptoms of rigidity and freezing of gait and is treated by the electrical stimulation therapy at the first time.

It is found that the rigidity can be obviously improved at the frequency B1 of 130 Hz and the freezing of gait can be improved at the frequency B2 of 80 Hz by using the single-frequency scan mode to apply constant frequency stimulation pulses at different frequencies to the target nerve tissue one by one.

Parkinson patient Y is then treated by a variable frequency stimulation pulses including a first frequency 80 Hz and a second frequency 130 Hz, wherein the electrical stimulation pulse trains at the first frequency or the second frequency has a time ratio of 50% and a duration of 20 seconds. After treating by the variable frequency stimulation pulses, it is found that freezing of gait is obviously improved, however, the rigidity is not obviously improved. So, the time ratio of the electrical stimulation pulse trains at 130 Hz is adjusted to 60%, and the time ratio of the electrical stimulation pulse trains at 80 Hz is adjusted to 40%. After treating by the adjusted variable frequency stimulation pulses, it is found that both the rigidity and the freezing of gait are obviously improved.

Case 3

Parkinson patient Z has the motor symptoms of rigidity and freezing of gait and is treated by constant frequency stimulation mode at the first time.

After applying a first constant frequency stimulation pulse of frequency 130 Hz, amplitude 2.7 V, and pulse width 60 μs, on left subthalamic nucleus and applying a second constant frequency stimulation pulse of frequency 130 Hz, amplitude 1.7 V, and pulse width 60 μs, on right subthalamic nucleus, the rigidity is obviously improved, however, the freezing of gait worsen. If the first constant frequency stimulation pulse of 130 Hz is adjusted to 60 Hz and other parameters are unchanged, the freezing of gait is obviously improved; however, the rigidity worsens.

Then Parkinson patient Z is treated with variable frequency stimulation mode. After applying a first variable frequency stimulation pulse of frequencies 60 Hz & 130 Hz, amplitude 2.7 V, and pulse width 60 μs, on left subthalamic nucleus and applying a second variable frequency stimulation pulse of frequencies 60 Hz & 130 Hz, amplitude 2.7 V, and pulse width 60 μs, on right subthalamic nucleus, both the rigidity and the freezing of gait are obviously improved. Each pulse train periods 151 has a duration of about 50 s. The electrical stimulation pulse train 152 at 60 Hz has a duration of 20 s, and the electrical stimulation pulse train 152 at 130 Hz has a duration of 30 s. Table 2 is a comparison of gait evaluation between constant frequency stimulation and variable frequency stimulation. Table 2 shows that compared with constant frequency stimulation, the variable frequency stimulation allows the Parkinson patient Z take less time to start walking and turning.

TABLE 2

Comparison of Gait evaluation

| | Constant frequency 130 Hz | Variable frequency 60 Hz&130 Hz |
|---|---|---|
| Typical start hesitation episode(s) | 20 | 3 |
| typical turning hesitation time(s) | 14 | 3 |
| Velocity(m/s) | 0.75 | 0.83 |
| Stride length(m) | 0.40 | 0.42 |
| FOG-Q Score | 20 | 8 |
| UPDRS III gait subscore (item 30) | 2 | 0 |

The embodiments shown and described above are only examples. Even though numerous characteristics and advantages of the present technology have been set forth in the forego description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

Depending on the embodiment, certain of the steps of methods described may be removed, others may be added, and the sequence of steps may be altered. The description and the claims drawn to a method may include some indication in reference to certain steps. However, the indication used is only to be viewed for identification purposes and not as a suggestion as to an order for the steps.

What is claimed is:

1. An electrical stimulation therapy method for neurological disease of a patient, the method comprising:
    implanting a lead in a brain of the patient so that at least one stimulation contactor of the lead in direct contact contact with a target nerve tissue of the patient, wherein the patient is a Parkinson patient adapting to a constant frequency stimulation pulse previously applied thereto and suffering from a motor symptom and a non-motor symptom;
    coupling the lead to a pulse generator; and
    applying a variable frequency stimulation pulse in a combination of at least two kinds of electrical stimulation pulse trains at different frequencies to target nerve tissue of the patient by the pulse generator and the lead; the at least two kinds of electrical stimulation pulse trains alternately stimulating the target nerve tissue and forming a plurality of pulse train periods; each of the at least two kinds of electrical stimulation pulse trains in each of the plurality of pulse train periods has a duration in a range from about 0.1 seconds to about 60 minutes; wherein the variable frequency stimulation pulse discourages or eliminates the non-motor symptom, and prevents the Parkinson patient from adapting to the constant frequency stimulation pulse on the condition of improving the motor symptom;
    wherein the target nerve tissue comprises subthalamic nucleus; the at least two kinds of electrical stimulation pulse trains comprise a first electrical stimulation pulse train with a first frequency in a range from about 90 Hz to about 250 Hz for improving the motor symptom selected from the group consisting of tremors and rigidity and a second electrical stimulation pulse train with a second frequency in a range from about 10 Hz to about 90 Hz for discouraging the non-motor symptom selected from the group consisting of dysarthria, freezing of gait and dyskinesia.

2. The method of claim 1, further comprising adjusting an amplitude of the variable frequency stimulation pulse, wherein the amplitude is adjusted in a range from about 0 V to about 10 V at a voltage mode; or the amplitude is adjusted in a range from about 0 mA to about 10 mA at a current mode.

3. The method of claim 2, wherein the adjusting the amplitude of the variable frequency stimulation pulse comprises making the first electrical stimulation pulse train and the second electrical stimulation pulse train have different amplitudes.

4. The method of claim 1, further comprising adjusting a pulse width of the variable frequency stimulation pulse, wherein the pulse width is adjusted in a range from about 0 μs to about 1000 μs.

5. The method of claim 4, wherein the adjusting the pulse width of the variable frequency stimulation pulse comprises making the first electrical stimulation pulse train and the second electrical stimulation pulse train have different pulse widths.

6. The method of claim 1, further comprising adjusting a time ratio of the first electrical stimulation pulse train and the second electrical stimulation pulse train.

7. The method of claim 1, further comprising optimizing at least one of the first frequency and the second frequency by a frequency scan function of the pulse generator.

8. The method of claim 1, wherein the duration is in a range from about 0.1 seconds to about 30 minutes; a quantity of the at least two kinds of electrical stimulation pulse trains is N, wherein $2 \leq N < 10$; and a time ratio of each of the at least two kinds of electrical stimulation pulse trains is greater than 5%.

9. The method of claim 8, wherein the duration is in a range from about 3 seconds to about 60 seconds; the frequency of each of the at least two kinds of electrical stimulation pulse trains is in a range from about 50 Hz to about 150 Hz; N=2 or 3; and the time ratio of each of the at least two kinds of electrical stimulation pulse trains is greater than 10%.

10. The method of claim 1, wherein there is a time space between adjacent two electrical stimulation pulse trains or between adjacent two pulse train periods, and the time space is in a range from about 0.01 seconds to about 60 minutes.

11. The method of claim 1, wherein an order of the at least two kinds of electrical stimulation pulse trains in each of the plurality of pulse train periods is from high frequency to low frequency, from low frequency to high frequency, or at random.

12. The method of claim 1, wherein the Parkinson patient had been treated by a first constant frequency stimulation pulse for a long time and still has non-motor symptoms; and the first frequency and the second frequency are determined by a method comprising
    the first constant frequency stimulation pulse is recorded as frequency A;
    the Parkinson patient is applied with different second constant frequency stimulation pulses until one of the non-motor symptoms is discouraged;
    the second constant frequency stimulation pulse on which the one of the non-motor symptoms is discouraged is recorded as frequency B;
    a frequency C is calculated by the formula $C=A^2/B$; and
    the frequency B and frequency C are used as the first frequency and the second frequency.

13. The method of claim 1, wherein the Parkinson patient had been treated by a first constant frequency stimulation pulse for a long time and still has non-motor symptoms; and the first frequency and the second frequency are determined by a method comprising:
    the first constant frequency stimulation pulse is recorded as frequency A;
    the Parkinson patient is applied with different second constant frequency stimulation pulses until one of the non-motor symptoms is discouraged;
    the second constant frequency stimulation pulse on which the one of the non-motor symptoms is discouraged is recorded as frequency B;
    a frequency C is calculated by the formula $C=2A-B$; and
    the frequency B and frequency C are used as the first frequency and the second frequency.

14. The method of claim 1, wherein an order of the at least two kinds of electrical stimulation pulse trains in each of the plurality of pulse train periods is random.

15. An electrical stimulation therapy method for neurological disease of a patient, wherein the patient is a Parkinson patient adapting to a constant frequency stimulation pulse previously applied thereto and suffering from a motor symptom and a non-motor symptom, the method comprising:

applying a variable frequency stimulation pulse to target nerve tissue of the patient, wherein the variable frequency stimulation pulse comprises at least two kinds of electrical stimulation pulse trains at different frequencies and the at least two kinds of electrical stimulation pulse trains alternately stimulate the target nerve tissue; the tartlet nerve tissue comprises subthalamic nucleus; the at least two kinds of electrical stimulation pulse trains comprises a first electrical stimulation pulse train with a first frequency in a range from about 90 Hz to about 250 Hz and a second electrical stimulation pulse train with a second frequency in a range from about 10 Hz to about 90 Hz; the first electrical stimulation pulse train is configured to improve the motor symptom selected from the group consisting of tremors and rigidity; the second electrical stimulation pulse train is configured to discourage the non-motor symptom selected from the group consisting of dysarthria, freezing of gait and dyskinesia; and the variable frequency stimulation pulse is configured to discourage or eliminate the non-motor symptom, and prevent the Parkinson patient from adapting to the constant frequency stimulation pulse on the condition of improving the motor symptom.

16. An implantable medical device for treating a patient, comprising:

a lead configured to apply a variable frequency stimulation pulse to target nerve tissue of a patient;

a pulse generator configured to generate the variable frequency stimulation pulse and deliver the variable frequency stimulation pulse to the lead, wherein the pulse generator has a frequency scan function; when a frequency scan range is set as F1min~F1max, a scan precision is set as S1, and a scar time is set as T1; the pulse generator generates a plurality of constant frequency stimulation pulses one by one at the frequencies of F1min, F1min+S1, F1min+2S1, F1min+3S1 . . . F1min+nS1 and F1max, wherein n is natural number and satisfies the formula: n≤(F1max−F1min)/S1; and each of the plurality of constant frequency stimulation pulses has an entire duration of T1; and a programmer configured to control the pulse generator; wherein the variable frequency stimulation pulse comprises at least two kinds of electrical stimulation pulse trains at different frequencies; the at least two kinds of electrical stimulation pulse trains alternately stimulate the target nerve tissue and form a plurality of pulse train periods; and each of the at least two kinds of alternate electrical stimulation pulse trains in each of the plurality of pulse train periods has a duration in a range from about 0.1 seconds to about 60 minutes.

17. The implantable medical device of claim 16, wherein the pulse generator further has a frequency scan function; when a frequency scan range is set as F2min~F2max, a scan precision is set as S2, and a scan time is set as T2; the pulse generator generates a plurality of variable frequency stimulation pulses one by one at the frequency combinations of "F2min and F2max", "F2min+S2 and F2max−S2", "F2min+2S2 and F2max−2S2" . . . and "F2min+nS2 and F2max−nS2", wherein n is natural number and satisfies the formula: n<(F2max−F2min)/2S2; and each of the plurality variable frequency stimulation pulses has an entire duration of T2.

18. The implantable medical device of claim 16, wherein the pulse generator further has a frequency scan function; when base frequencies are set as Fb1 and Fb2, a scan range is set as F3, a scan precision is set as S3, and a scan time is set as T3; the pulse generator generates a plurality of variable frequency stimulation pulses one by one at the frequency combinations of "Fb1 and Fb2", "Fb1+S3 and Fb2", "Fb1+2S3 and Fb2" . . . "Fb1+nS3 and Fb2", "Fb1−S3 and Fb2", "Fb1−2S3 and Fb2" . . . "Fb1−nS3 and Fb2", "Fb1 and Fb2+S3", "Fb1 and Fb2+2S3" . . . "Fb1 and Fb2+nS3", "Fb1 and Fb2−S3", "Fb1 and Fb2−2S3" . . . and "Fb1 and Fb2−nS3", wherein n is natural number and satisfies the formula: n=F3/S3; and each of the plurality variable frequency stimulation pulses has an entire duration of T3.

19. The implantable medical device of claim 16, wherein the pulse generator further has a frequency scan function; when base frequencies are set as Fb1 and Fb2, a scan range is set as F3, a scan precision is set as S3, and a scan time is set as T3; the pulse generator generates a plurality of variable frequency stimulation pulses one by one at the frequency combinations of "Fb1 and Fb2", "Fb1+S3 and Fb2+S3", "Fb1+2S3 and Fb2+2S3" . . . "Fb1+nS3 and Fb2+nS3", "Fb1−S3 and Fb2−S3", "Fb1−2S3 and Fb2−2S3" . . . "Fb1−nS3 and Fb2−nS3", "Fb1+S3 and Fb2−S3", "Fb1+2S3 and "Fb2−2S3" . . . "Fb1+nS3 and Fb2−nS3", "Fb1−S3 and Fb2+S3", "Fb1−2S3 and Fb2+2S3", . . . and "Fb1−nS3 and Fb2+nS3", wherein n is natural number and satisfies the formula: n=F3/S3; and each of the plurality variable frequency stimulation pulses has an entire duration of T3.

20. An implantable medical device for treating a patient, comprising:

a lead configured to apply a variable frequency stimulation pulse to target nerve tissue of a patient;

a pulse generator configured to generate the variable frequency stimulation pulse and deliver the variable frequency stimulation pulse to the lead, wherein the pulse generator has a frequency scan function; when a frequency scan range is set as F2min~F2max, a scan precision is set as S2, and a scan time is set as T2; the pulse generator generates a plurality of variable frequency stimulation pulses one by one at the frequency combinations of "F2min and F2max", "F2min+S2 and F2max−S2", "F2min+2S2 and F2max−2S2" . . . and "F2min+nS2 and F2max−nS2", wherein n is natural number and satisfies the formula: n<(F2max−F2min)/2S2; and each of the plurality variable frequency stimulation pulses has an entire duration of T2; and a programmer configured to control the pulse generator; wherein the variable frequency stimulation pulse comprises at least two kinds of electrical stimulation pulse trains at different frequencies; the at least two kinds of electrical stimulation pulse trains alternately stimulate the target nerve tissue and form a plurality of pulse train periods; and each of the at least two kinds of alternate electrical stimulation pulse trains in each of the plurality of pulse train periods has a duration in a range from about 0.1 seconds to about 60 minutes.

21. An implantable medical device for treating a patient, comprising:

a lead configured to apply a variable frequency stimulation pulse to target nerve tissue of a patient;

a pulse generator configured to generate the variable frequency stimulation pulse and deliver the variable frequency stimulation pulse to the lead, wherein the pulse generator has a frequency scan function; when base frequencies are set as Fb1 and Fb2, a scan range is set as F3, a scan precision is set as S3, and a scan time is set as T3; the pulse generator generates a plurality of variable frequency stimulation pulses one by one at the frequency combinations of "Fb1 and Fb2", "Fb1+S3 and Fb2", "Fb1+2S3 and Fb2" ... "Fb1+nS3 and Fb2", "Fb1−S3 and Fb2", "Fb1−2S3 and Fb2" ... "Fb1−nS3 and Fb2", "Fb1 and Fb2+S3", "Fb1 and Fb2+2S3" ... "Fb1 and Fb2+nS3", "Fb1 and Fb2−S3", "Fb1 and Fb2−2S3" ... and "Fb1 and Fb2−nS3", wherein n is natural number and satisfies the formula; n=F3/S3; and each of the plurality variable frequency stimulation pulses has an entire duration of T3; and a programmer configured to control the pulse generator; wherein the variable frequency stimulation pulse comprises at least two kinds of electrical stimulation pulse trains at different frequencies; the at least two kinds of electrical stimulation pulse trains alternately stimulate the target nerve tissue and form a plurality of pulse train periods; and each of the at least two kinds of alternate electrical stimulation pulse trains in each of the plurality of pulse train periods has a duration in a range from about 0.1 seconds to about 60 minutes.

22. An implantable medical device for treating a patient, comprising;

a lead configured to apply a variable frequency stimulation pulse to target nerve tissue of a patient;

a pulse generator configured to generate the variable frequency stimulation pulse and deliver the variable frequency stimulation pulse to the lead, wherein the pulse generator has a frequency scan function; when base frequencies are set as Fb1 and Fb2, a scan range is set as F3, a scan precision is set as S3, and a scan time is set as T3; the pulse generator generates a plurality of variable frequency stimulation pulses one by one at the frequency combinations of "Fb1 and Fb2", "Fb1+S3 and Fb2+S3", "Fb1+2S3 and Fb2+2S3" ... "Fb1+nS3 and Fb2+nS3", "Fb1−S3 and Fb2−S3", "Fb1−2S3 and Fb2−2S3" ... "Fb1−nS3 and Fb2−nS3", "Fb1+S3 and Fb2−S3", "Fb1+2S3 and Fb2−2S3" ... "Fb1+nS3 and Fb2−nS3", "Fb1−S3 and "Fb2+S3", "Fb1−2S3 and Fb2+2S3", ... and "Fb1−nS3 and Fb2+nS3", wherein n is natural number and satisfies the formula: n=F3/S3; and each of the plurality variable frequency stimulation pulses has an entire duration of T3; and a programmer configured to control the generator; wherein the variable frequency stimulation pulse comprises at least two kinds of electrical stimulation pulse trains at different frequencies; the at least two kinds of electrical stimulation pulse trains alternately stimulate the target nerve tissue and form a plurality of pulse train periods; and each of the at least two kinds of alternate electrical stimulation pulse trains in each of the plurality of pulse train periods has a duration in a range from about 0.1 seconds to about 60 minutes.

\* \* \* \* \*